United States Patent
Kippenhan, Jr.

(10) Patent No.: US 6,793,880 B2
(45) Date of Patent: Sep. 21, 2004

(54) APPARATUS AND METHOD FOR MONITORING BIOFILM CLEANING EFFICACY

(75) Inventor: Roland C. Kippenhan, Jr., Woodbury, MN (US)

(73) Assignee: Minntech Corporation, Minneapolis, MN (US)

( * ) Notice: Subject to any disclaimer, the term of this patent is extended or adjusted under 35 U.S.C. 154(b) by 404 days.

(21) Appl. No.: 09/905,034

(22) Filed: Jul. 13, 2001

(65) Prior Publication Data
US 2003/0012688 A1 Jan. 16, 2003

(51) Int. Cl.⁷ .................................................. A61L 2/00
(52) U.S. Cl. ........................ 422/3; 422/1; 422/26; 422/28; 422/292; 435/29; 435/289.1; 435/970
(58) Field of Search .......................... 422/292, 3, 1, 422/26, 28; 435/29, 289.1, 970, 4, 31

(56) References Cited

U.S. PATENT DOCUMENTS

| | | | |
|---|---|---|---|
| 4,912,332 A | 3/1990 | Siebel et al. | |
| 5,349,874 A | 9/1994 | Schapira et al. | |
| 5,487,981 A | 1/1996 | Nivens et al. | |
| 5,736,355 A | 4/1998 | Dyke et al. | |
| 5,882,589 A | 3/1999 | Mariotti | |
| 5,923,432 A | 7/1999 | Kral | |
| 5,928,889 A * | 7/1999 | Bakich et al. | 435/29 |
| 5,928,948 A | 7/1999 | Malchesky | |
| 6,051,423 A | 4/2000 | Ceri et al. | |
| 6,068,815 A | 5/2000 | Oberleitner et al. | |
| 6,156,267 A | 12/2000 | Pai et al. | |
| 6,394,111 B1 | 5/2002 | Jacobs et al. | |
| 6,428,746 B1 * | 8/2002 | Muscarella et al. | 422/3 |
| 6,454,871 B1 * | 9/2002 | Labib et al. | 134/8 |
| 6,589,481 B1 * | 7/2003 | Lin et al. | 422/33 |
| 2003/0164182 A1 | 9/2003 | Jacobs | |

OTHER PUBLICATIONS

Brochure on TOSI Info (Test Object Surgical Instruments); Pereg GmbH.
Chapter 75: Biocide Susceptibility Testing of Biofilms Authors: Howard Ceri, Douglas W. Morck, and Merie E. Olson.

* cited by examiner

Primary Examiner—Krisanne Jastrzab
(74) Attorney, Agent, or Firm—Merchant & Gould P.C.

(57) ABSTRACT

Methods and devices for determining the efficacy of a cleaning, disinfecting, or sterilizing process intended to remove biofilms are provided. The devices involve a biofilm sample, a biofilm indicator, and a simulated endoscope.

30 Claims, 4 Drawing Sheets

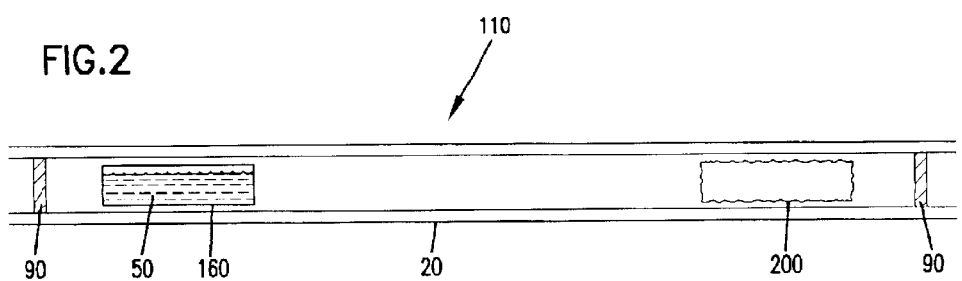
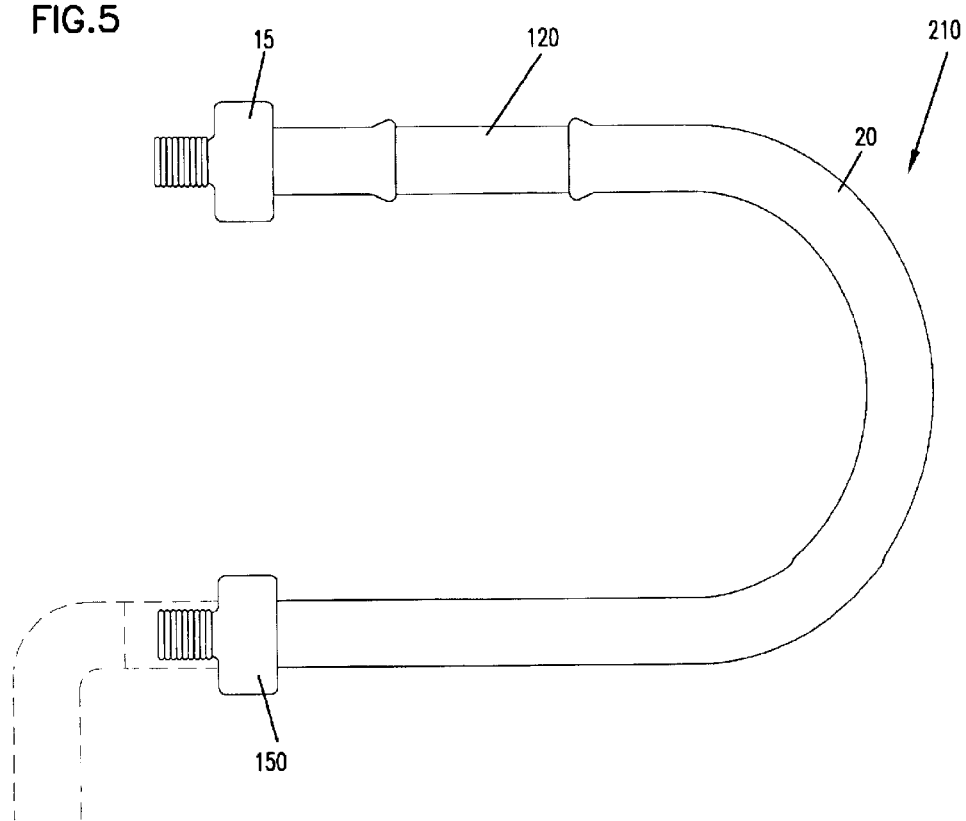

APPARATUS AND METHOD FOR MONITORING BIOFILM CLEANING EFFICACY

FIELD OF THE INVENTION

The present invention relates generally to monitoring the cleaning, disinfecting, and sterilizing of instruments and equipment. More particularly, the present invention relates to methods and devices for monitoring the efficacy of which medical devices are cleaned, disinfected, or sterilized.

BACKGROUND OF THE INVENTION

Known methods for disinfecting or sterilizing medical devices for re-use have historically used high pressure steam to render the surfaces of a medical device free of all forms of viable microorganisms (sterilization) or free from microorganisms except spore forming microorganisms (high level disinfection). In the last 40 years, medical devices have become more complex with respect to design and materials that are heat sensitive. Newer low temperature disinfection methods have accordingly been developed including ethylene oxide gas, vapor phase hydrogen peroxide, vapor phase peracetic acid and liquid disinfectants such as glutaraldehyde and peracetic acid solutions for reprocessing heat sensitive devices. However, many medical instruments are made of materials that may be damaged by exposure, especially repeated exposure, to high-pressure steam or gaseous disinfection procedures.

Devices that automatically clean and then disinfect medical and other equipment have been developed. Typically, these systems simply carry out a wash cycle for a preset duration. Cleaning is not always certain, especially when the water is not at the ideal temperature, the detergent is not at full strength, water pressure is abnormally low, the cleaning cycle is aborted due to an ineffective timing device, or if other error conditions are present.

One error condition is the failure to reduce the biological burden on incoming devices to an acceptable level. All health care reprocessing guidelines call for the precleaning of medical devices by a manual process that can reduce the bioburden level by 3 logs. Without a consistent manual precleaning process, any subsequent disinfection and sterilization is likely to fail. This is probably the greatest source of variability in the overall reprocessing sequence.

One particular class of medical devices, flexible endoscopes, has advanced the ability of medial practitioners for diagnosis but has also proved more difficult to adequately clean. Endoscopes are protectively encased bundles of flexible optical fibers used to transmit images to the operator at one end from otherwise inaccessible regions into which the opposite end of the instrument is inserted, so as to obtain a view of the structures surrounding such regions. Such an arrangement makes possible the visual examination, and even photographing, of structures surrounding cavities to which there is some external access, such access typically being a relatively small opening at some distance from the region of interest.

Endoscopes typically include means for allowing insertion of fluids into the region of interest and means for removal of tissue. Thus, in addition to the fiber optic bundle, there is usually provided a plurality of enclosed channels or passageways more or less paralleling the direction of the fiber optic bundle. These channels are also included within the enclosure that protects the fiber optic bundle. Specifically, such channels are typically provided to carry one or more of water, air, and carbon dioxide gas. A further channel is often provided to permit the extension therethrough of the instrumentation needed to conduct a biopsy of tissue in the region of interest. This latter channel may also be connected to a vacuum source as a means for obtaining fluid samples. This biopsy/suction source typically has a larger diameter than the other channels.

Because endoscopes are complex, highly instrumented medical devices, they are too costly to be disposable. Therefore, it is desirable to reuse such devices. Because they are exposed to bodily fluids and tissue, both internally and externally, it is necessary to clean these devices thoroughly before reuse.

Automated endoscopic reprocessors have been developed specifically to clean and disinfect flexible endoscopes to a level that mitigates the transmission of pathogenic organisms and disease between patients who are subject to an endoscopic procedure. U.S. Pat. No. 4,763,678, which is hereby incorporated by reference, discloses an exemplary endoscope reprocessor.

Automated endoscopic reprocessors (AERs) have significantly advanced the state of the art of reprocessing complex medical devices. Prior to the development of AER's, flexible endoscopies were cleaned and disinfected in an uncontrolled manual process of cleaning, disinfecting and rinsing in disinfectant. AER's provide an environment wherein the critical reprocessing parameters of liquid disinfectant use-life, rinse volumes, disinfectant contact time, disinfectant temperature and disinfectant volumes are controlled. The effectiveness of marketed disinfectants are carefully controlled by government regulatory agencies requiring scientific data related to the ability of the disinfectant to kill pathogenic under challenging conditions and related to the ability of AER's to deliver legally marketed disinfectants to the flexible endoscope being reprocessed.

U.S. Pat. No. 6,068,815 describes a chemical concentration detector using infrared light to determine concentration of the active agent. Monitoring of liquid chemical disinfection or sterilization can also be carried out by measuring the physical parameters of a reprocessing device as described in U.S. Pat. No. 6,156,267. When acceptable parameter levels have been met, the processed load is assumed to be disinfected or sterilized thus claiming to eliminate the need for biological indicators and chemical indicators or integrators. A drawback of this monitoring approach is that it fails to account for the variability associated with the type, resistance or amount of biological organisms that might be present in the medical device being reprocessed.

An additional method of monitoring the effectiveness of a particular disinfectant is through the use of biological indicators. Biological indicators are typically strips of paper or other porous media containing a controlled number of bacterial spores that provide a high level of challenge to the disinfectant process. Spores of *bacillus subtilis, bacillus circulans* and *bacillus stearotherophilus* have been used to monitor high-level disinfection processes including liquid disinfection and sterilization. A specific device to determine the effectiveness of a decontamination process with a self-contained biological indicator and a spore trapping microporous membrane is described in U.S. Pat. No. 5,736, 355. While this device is useful for determining spore survival in the presence of a disinfectant, it does not address the problem of monitoring biological activity or the absence of biological activity within a thin, narrow endoscope lumen.

While some AER manufacturers have developed either chemical or biological indicators, as described above, to monitor the effectiveness of a particular high-level disinfection AER process or cycle, their use is problematic. Existing chemical or biological indicators for AER's do not take into account the challenge introduced by long, narrow lumens that provide an environment wherein microorganisms are difficult remove and can easily colonize the entire endoscope.

A relatively new problem in reprocessing of flexible endoscopes is related to advances in our understanding of a new class of materials called "biofilms". Biofilms are microbiologically generated polysaccharide matrices that form when bacteria adhere to surfaces in aqueous environments and begin to excrete a slimy, glue like substance that can anchor them to all kinds of materials such as those found in medical devices and tissue. A biofilm can be formed by a single bacterial species, but more likely will consist of many species of bacteria, as well as fungi, algae, protozoa and inorganic products. Biofilms can form on any surface exposed to bacteria, nutrients and water under the right conditions. Many species of bacteria are becoming recognized as capable of existing in a free suspended state called the planktonic state or in a biofilm matrix referred to as the biofilm state. It is a characteristic of biofilms that the planktonic and non-planktonic states can be reversed under the right conditions. Once anchored to a surface, biofilm microorganisms can colonize and grow into a complex colony that contain and protect bacteria from outside attack.

Biofilms were first recognized as problematic in the industrial environment where fungi and algae can cause problems in cooling towers or water treatment and storage facilities. Recently, biofilms have become indicated as an infection control issue for implantable medical devices such as urinary catheters, implantable cardiac devices and cerebral shunts.

U.S. Pat. Nos. 5,928,948 and 5,923,432 describe a method for the assessment and validation of a cleaning process using a porous substrate containing contaminated soils and shielded from the environment by an impermeable layer. The cleaning process is evaluated by examining the porous material with an infrared or other electronic reader to determine the presence of remaining soil that has not been removed. The method ignores the problem of biofilm formation and only uses a challenge package in lieu of replicating the endoscope environment.

Several methods have recently been developed to form biofilms on projections by providing a flow of liquid growth medium across materials and assays made of the resulting biofilm as described in U.S. Pat. No. 6,051,423. While these methods do provide for the preparation and analysis of biofilm materials in a controlled laboratory environment they do not address the problem of biofilm removal and assay in the real world hospital environment involving reprocessable flexible endoscopes.

SUMMARY OF THE INVENTION

The present invention is directed to a cleaning efficacy indicator system and method that automatically assesses the cleaning in a real-time, cost-effective, and highly accurate manner. It is therefore an object of the invention to provide a device that monitors the ability of automated endoscopic reprocessors to remove bacterial biofilms within the long, narrow lumens of a flexible endoscope. The device is intended to provide a challenge to biofilm removal within a long, narrow environment that simulates the environment found within a flexible endoscope. It is a further object of the invention to utilize a biofilm detecting substance or dye that can be quantitatively analyzed within the challenge device without contaminating either the endoscope or the surrounding environment with either the planktonic or biofilm containing bacteria.

One aspect of the invention is to provide an apparatus that simulates the most difficult to clean lumens of a flexible endoscope. The simulated device is composed of endoscope lumen materials, approximating the length of flexible endoscope lumens but without the costly optical train of flexible endoscopes.

Another aspect of the invention is to provide an apparatus that is constructed of components that are optically transmissive and can be easily analyzed through an external optical analysis of internal biological activity.

A further aspect of the invention is to provide a device that can be connected into a flexible endoscopic reprocessor to evaluate cleaning effectiveness against biofilm challenge agents but without contamination of either the endoscope being reprocessed or the automated endoscopic reprocessor.

An additional aspect of the invention is to provide a device with a frangible chamber containing stains or dyes specific for biofilms. Said frangible chamber is contained within but separated from the simulated endoscope to release biofilm dyes when needed for analysis.

Another aspect of the invention is to provide an optical detector that is capable of quantitative detection of biofilm specific dyes or stains. Said detector is designed to fit and can be used either inside or outside of an automated endoscopic reprocessor.

One advantage of the present invention is to provide a flexible simulated endoscope that exactly simulates the physical environment and biological conditions of endoscope lumens and can be easily analyzed and cost effectively disposed of after analysis.

Another advantage of the present invention is to provide a biofilm containing simulated endoscope that can be immediately analyzed for biofilm activity after the simulated endoscope has been reprocessed either internal or external to an automated endoscope reprocessor.

A further advantage of the present invention is to provide a biofilm containing simulated endoscope that can be reprocessed without the risk of cross contamination of flexible endoscopes or the reprocessors with biofilm test substrates.

An additional advantage of the present invention is to deliver a biofilm indicating dye when needed to analyze for biofilm residuals after reprocessing.

BRIEF DESCRIPTION OF THE DRAWINGS

FIG. 2 is a longitudinal cross sectional view of a portion of another biofilm cleaning efficacy device in accordance with the principles of the present invention.

FIG. 5 is a top view of another embodiment of a biofilm cleaning efficacy device of the invention.

DETAILED DESCRIPTION

Figure 1:
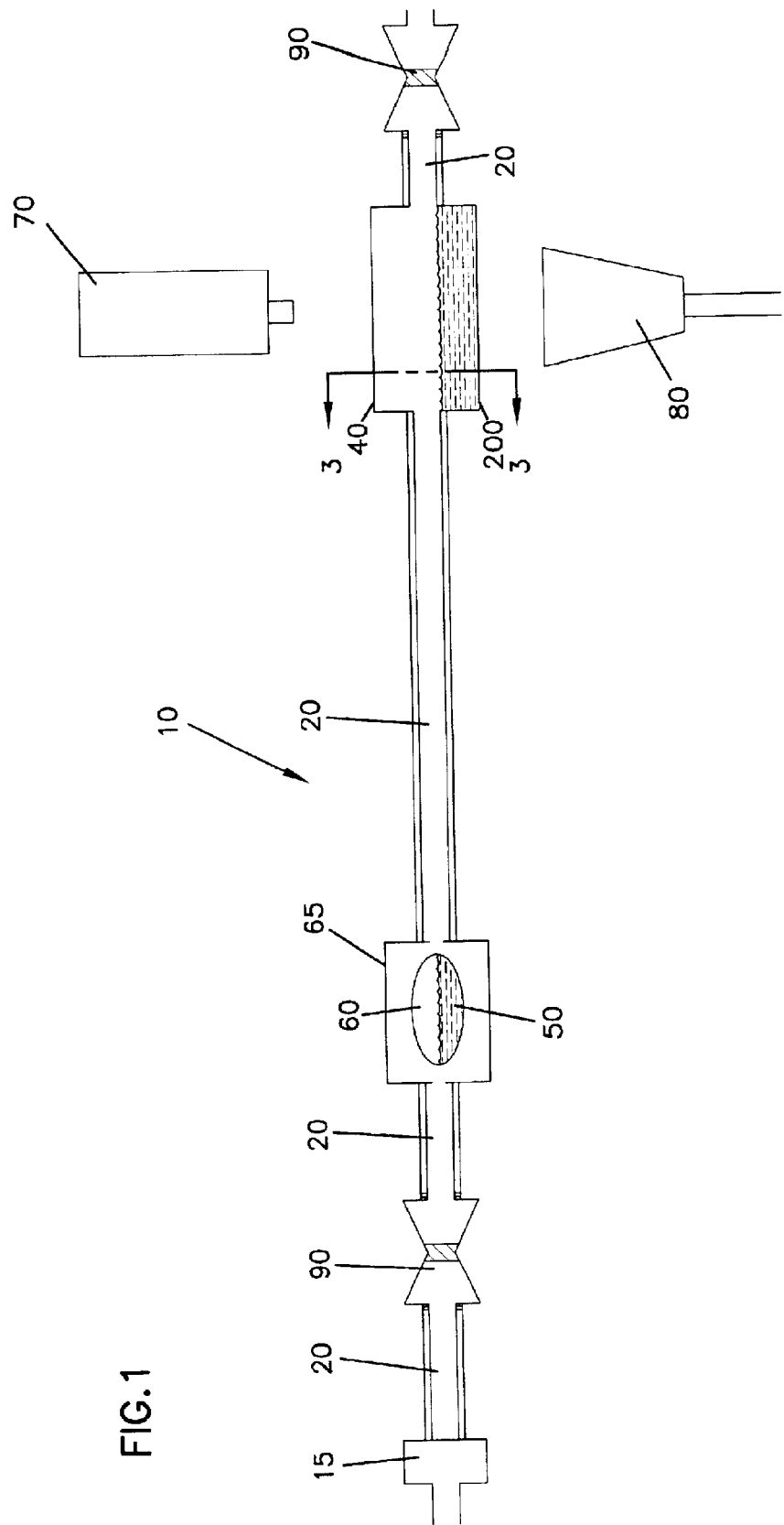
FIG. 1 is a longitudinal cross sectional view of one embodiment of a biofilm cleaning efficacy device of the invention.

The present invention has application in monitoring the cleaning of medical instruments and equipment, particularly instruments and devices involving fluid flow through a lumen (e.g., catheters, endoscopes or other devices for introducing or removing fluid from the body). The invention is specifically directed to monitoring the cleaning of endoscopes. The invention has particular application in monitoring the ability of automated endoscopic reprocessors to effectively reprocess by cleaning, high level disinfecting, or sterilizing flexible endoscopic medical devices to remove biofilm-containing deposits. The invention also has application for monitoring the cleaning of any implantable medical device. Almost any implantable medical device has the potential to develop biofilm communities and resultant disease complications. Cystic fibrosis, heart valve failures, and urinary infections are some specific complications attributed to biofilm formation. It will be appreciated, however, that the invention is also applicable to monitoring the cleaning of other articles such as food processing equipment, pharmaceutical equipment, dental equipment, aquarium equipment, water treatment systems, oil and gas pipelines and refining equipment, and any other equipment involving fluid flow. Biofilms are problematic within water lines from a water treatment plant to an end user as are biofilms on ship hulls.

As used herein, "biofilm-specific indicator" means any substance that binds or reacts with a biofilm and may be detected. For example, biofilm-specific indicators can be antibodies or other molecules that specifically bind a microorganism present in the biofilm, and that can be detected and measured. Microorganisms that may be present in a biofilm include bacteria, algae, fungi, and protozoa. Antibodies or other molecules that specifically bind non-living organic and inorganic products present in a biofilm may also be used as the biofilm-specific indicator. The antibodies or other biofilm-binding molecules are labeled. Labels include any substance that can be detected, such as fluorescent molecules and radioactive markers. Alternatively, the biofilm-specific indicator can be a stain or dye that binds or reacts with a microorganism, such as a bacterial strain, present in the biofilm, or with a product excreted or produced by the microorganism in the biofilm, such as a polysaccharide. A stain or dye can be fluorescent, phosphorescent or capable of optically absorbing light of a specific wavelength. As an example, crystal violet dye has an affinity for a broad spectrum of microorganisms and has a strong absorbance at 563 nm. Toluidine blue dye can be used as an alternate with a maximum absorbance at 540 nm. Other gram positive or gram negative live-dead bacteria stains known to those skilled in the art can be used to detect activity within the biofilm matrix.

As used herein, "simulated contaminated instrument" means a device that simulates the structure of an instrument to be cleaned and contains a source of contamination. The device may be a section of the actual instrument, for example, a section where contamination is a particular problem. The device may be constructed of the same materials as the instrument, or the device may be made of inexpensive, disposable materials that simulate, at least for cleaning purposes, the materials used to make the instrument. The source of contamination may be a viable or non-viable microorganism sample, organic material, biofilm environment simulating materials such as hydrogels or synthetic biofilms produced in a chemostat device, or any other contaminant that may be found in or on the instrument to be cleaned.

As used herein, "simulated endoscope," means a device that simulates the structure of an endoscope, including the internal environment. A simulated endoscope can be a length of tubing of the composition, size and length generally used in the manufacture of endoscopes. The tubing is preferably flexible and contains at least one lumen. Alternatively, a simulated endoscope can be an actual endoscope with the optical and mechanical components removed.

As used herein, "of a type used for endoscopes" refers to tubing, preferably plastic, that has a composition and size generally used in the manufacture of endoscopes. The tubing has at least one lumen, and can have multiple lumens to simulate more complex endoscopes.

As used herein, "disinfection" means the absence of pathogenic organisms, "sterilization" means the absence of all organisms, and "decontamination" means sterilization, disinfection, or both.

As used herein, "biofilm surrogate coating" means a coating containing one or more species of bacteria, fungi, algae, or protozoa, or combinations thereof, which simulates a biofilm. The selection of bacteria, fungi, algae, protozoa, or combinations thereof is based on the probable microorganism.

The cleaning efficacy system apparatus involves a simulated endoscope, a biofilm or biofilm surrogate coating in fluid communication with the simulated endoscope, a biofilm-specific indicator, and a means of detecting the biofilm-specific indicator. The simulated endoscope is generally a section of flexible tubing, although rigid tubing may also be used. The tubing is preferably transparent and of a type appropriate for the manufacture of endoscopes, although flexible, transparent tubing of any composition may be used. The tubing may have a length similar to that of a particular type of endoscope, or it may be shorter. For detecting residual biofilm based on optical density, the optical density of the tubing is known.

The biofilm or biofilm surrogate coating may be provided on the inner surface of the simulated endoscope. Alternatively, the biofilm may be provided on a support that fits inside the simulated endoscope. In another embodiment, the biofilm is provided on the inside of a small section of tubing that is attached to the simulated endoscope. In a further embodiment, the biofilm is provided on a support that fits inside a small section of tubing that is attached to the simulated endoscope.

The biofilm may be produced in any manner using one or more species of microorganisms, generally bacteria. The biofilm is generally produced by culturing the bacteria under conditions in which a liquid bacterial culture flows across a stationary surface. When the biofilm is to be present on the inside of the simulated endoscope or on the inside of a small section of tubing, the liquid bacterial culture will generally be passed through the tubing to create the biofilm. A biofilm may be created on a support that is then placed inside the simulated endoscope or small section of tubing. One example of a method of producing biofilm on multiple solid supports is disclosed in U.S. Pat. No. 6,051,423 of Ceri et al. Ceri et al. produce a biofilm on projections across which a liquid bacterial culture flows. The individual projections may be removed for testing.

A second example of a method of producing a biofilm on a solid support is outlined in American Society of Testing and Materials draft document on Standard Test Method for Growing a *Pseudomonas aeruginosa* Biofilm with Shear and Continuous Flow using a Rotating Disk Reactor. This test method is used for growing a repeatable biofilm in a rotating disk reactor. The biofilm is established by operating the reactor in batch for 24 hours. Steady state growth is reached while the reactor operates for an additional 24 hours with continuous flow of nutrients. The residence time of the nutrients in the reactor is set so as to select for biofilm growth, and is species and reactor parameter specific. During the entire 48 hours, the biofilm experiences continuous fluid shear from rotation of the disk.

Biofilm-coated supports, such as the projections of Ceri et al, or other solid supports on which a biofilm has been created, are placed inside the simulated endoscope or small section of tubing.

The biofilm may be made up of any bacterial species, and may additionally include fungi, algae, and any other microorganism. Alternatively, the biofilm may be made up of one or more fungus species, without any bacteria. Examples of fungal biofilms include those made from Candida and Aspergillus species. In a preferred embodiment, the biofilm is made up of bacterial species that are often present in the contaminated instrument. One example of a biofilm for determining the cleaning efficacy in medical endoscopes is a combination of *Escherichia coli* and *Pseudomonas aeruginosa*. Other species of bacteria that may be used for preparing the biofilm include *Staphylococcus epidermidis, Staphylococcus aureus, Legionella pneumophila, Bacillus subtilis*, Cholera sp., *Saccharomyces cerivisae, Enterococcus faecalis,* and any other bacteria that might be present in a contaminated instrument to be cleaned.

The biofilm-specific indicator may be any molecule, compound, composition, or marker that binds or otherwise labels the biofilm. The indicator may bind or label either or both of the microorganism and chemical compounds making up the extracellular matrix. When more than one species of microorganism makes up the biofilm, the indicator may bind one or many species, or multiple different indicators, each specific to one species of microorganism, may be used. Additionally, an indicator specific to a species of microorganism may be mixed with an indicator specific to a chemical compound present in the extracellular matrix. Examples of biofilm-specific indicators that could be considered for the instant device include labeled antibodies, gram positive stains, gram negative stains and green fluorescent stains. This class of indicators has advantages in that they are readable with simple spectorphotometric analysis. More complex and expensive methods of detection include conventional light microscopy, electron scanning microscopy, transmission microscopy, epi fluorescent microscopy, confocal scanning laser microscopy and molecular probe microscopy.

For use in a simulated endoscope or other lumen-containing instrument, the biofilm-specific indicator may be provided, for example, in a frangible vial inside or in fluid communication with the simulated endoscope or instrument lumen.

The method for assessing and evaluating a cleaning process designed for cleaning an instrument involves processing a simulated contaminated instrument according to the cleaning process being monitored, and detecting the presence and/or amount of any remaining contaminant. The presence and/or amount of residual contaminant in or on the simulated instrument after the cleaning process is indicative of the efficacy of the cleaning process. In one embodiment, the instrument is considered clean when the amount of contamination remaining after the cleaning process falls below a predetermined level. The simulated contaminated instrument provides a means of determining the cleaning efficacy under conditions as close as possible to the actual cleaning of the instrument.

In one embodiment of the invention, the contamination is a biofilm. Since biofilms form under conditions involving fluid flow and are often present in instruments containing tubing, using a section of tubing or other device with a lumen containing a biofilm as the cleaning indicator provides an improved indication of the efficacy of the cleaning process. This is especially important in the cleaning of endoscopes.

One embodiment of a biofilm cleaning efficacy device 10 for use with an endoscope reprocessor is shown in FIG. 1. The device involves, connected in series from one end to the other end and separated by one or more lengths of tubing 20, a hookup connector 15 for attaching the device to a reprocessor, a porous filter element 90, a biofilm-specific indicator chamber 60 containing a biofilm-specific indicator 50, a biofilm chamber 40 containing a biofilm 200, and another porous filter element 90. The tubing has an inner diameter of about 1.0 mm to about 6.0 mm. The tubing 20 can be made of transparent, flexible plastic, or any other material suitable for the manufacture of endoscopes. The biofilm-specific indicator chamber 60 is adapted and positioned to allow cleaning fluids to pass around the indicator chamber, through the tubing 20 and into the biofilm chamber. The overall length of the device is preferably from about 55 cm to about 250 cm. The biofilm-specific indicator chamber 60 contains an indicator 50 that binds or otherwise reacts with and labels the biofilm in the biofilm chamber 40. The filter elements 90 prevent microorganisms in the biofilm from exiting the cleaning efficacy device 10. The device also includes a separate light emitting source 70 and light detector 80 positioned adjacent the biofilm chamber 40. The light source 70 and detector 80 are selected for their ability to detect and/or measure the biofilm-specific indicator 50.

In one embodiment, the biofilm-specific indicator chamber 60 is a frangible chamber containing the indicator 50. The frangible chamber can be made of glass, or other easily crushed material. The frangible chamber has an outer covering 65 that protects the user and keeps the crushed glass and the contents of the chamber within the cleaning efficacy device.

One embodiment of a method for assessing and evaluating a cleaning process intended to disinfect, sterilize, or decontaminate items to be cleaned involves the following steps. A support (e.g., the wall of chamber 40 or a separate support such as support 300 shown in FIG. 4) is contaminated with a known biofilm 200. The support generates at least one support spectral band and the biofilm 200 generates at least one biofilm spectral band when illuminated by light in the infrared or ultraviolet range. The support and the biofilm 200 are subjected to the cleaning process to be assessed and evaluated. The cleaning process is assessed by evaluating the support for remaining biofilm by spectroscopic analysis. The spectroscopic analysis includes illuminating the support with light in the infrared or ultraviolet range using light source 70, and receiving infrared or ultraviolet light reflected from the support in light detector 80. An electrical signal is then generated, which is indicative of the support and the remaining biofilm. The components of the electrical signal attributable to the support spectral band and the biofilm spectral band are separated and analyzed. An output display representative of residual biofilm remaining on the support after the cleaning process is then generated. When the amount of biofilm detected falls below a predetermined level, the cleaning process is complete.

In use, the hookup connector 15 on the device shown in FIG. 1 is connected to a port of an endoscope reprocessor. For real-time evaluation of a cleaning process, contaminated endoscopes are also connected to the endoscope reprocessor and are subjected to the same cleaning process as the biofilm cleaning efficacy device. Once the cleaning process has been run, the frangible indicator chamber 60 is crushed, allowing the indicator to travel down the tubing 20 to the biofilm chamber 40. A washing step can then be performed to remove unbound indicator. The light source 70 is positioned to direct light through the biofilm chamber 40 to the detector 80. The presence of any remaining biofilm is detected based on the properties of the biofilm indicator and the light source. The absence of biofilm in the biofilm chamber after a cleaning process means the process was effective. The presence and/or amount of biofilm after the cleaning process indicates the cleaning process is not effective in removing biofilm contamination.

In the embodiment of the device 10 shown in FIG. 1, the frangible biofilm-specific indicator chamber 60, the biofilm chamber 40, and the filters 90 are separate elements connected to each other with lengths of tubing 20. In this embodiment, the biofilm-specific indicator chamber 60 is configured to allow cleaning fluids to pass through. In alternative embodiments, these elements can all be contained within a single length of tubing, as shown in FIG. 2, or some of the elements can be separate and some contained within the tubing, as shown in FIG. 5.

FIG. 2 shows a cross-section of an embodiment of a biofilm cleaning efficacy device 110 in which a frangible biofilm-specific indicator chamber 160, biofilm 200, and filter elements 90 are inside tubing 20. The indicator chamber 160 contains a biofilm-specific indicator 50 and is sized such that cleaning fluids can pass around the indicator chamber 160. Upon breaking or crushing the indicator chamber 160, the biofilm-specific indicator 50 flows inside the tubing 20 to the biofilm 200. The indicator labels any biofilm present.

Figure 4:
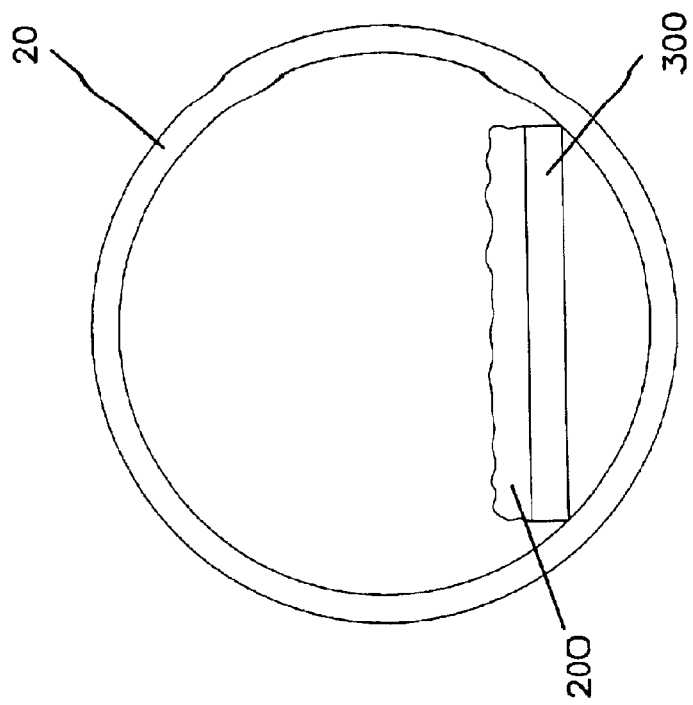
FIGS. 3 and 4 are cross-sectional views taken along line 3—3 of FIG. 1, showing alternative embodiments of the biofilm coating portion of the invention.
Figure 3:
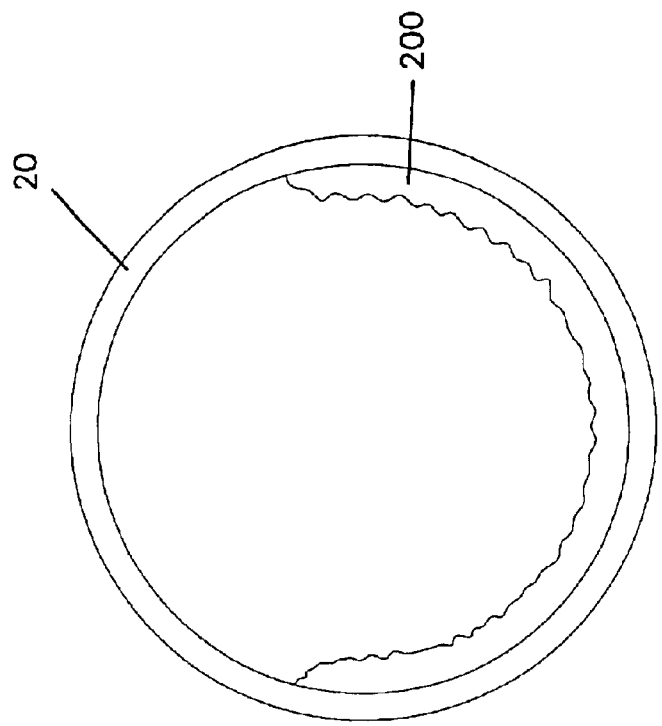

FIGS. 3 and 4 show cross-sections through the biofilm chamber 40 of FIG. 1. In the embodiment shown in FIG. 3, a biofilm 200 is located on an inner surface of the tubing 20. In this embodiment, the biofilm is created on the interior of the tubing 20. A liquid bacterial culture is passed through the tubing under conditions sufficient for growth of a biofilm. In an alternative embodiment, a removable section of tubing 120 having a biofilm on an interior surface is connected to the tubing 20 of the device (FIG. 5).

In the embodiment of FIG. 4, a biofilm 200 is located on support 300 that is placed inside the tubing 20. The support can be any material on which a biofilm can be grown, such as plastic, steel, or titanium. The support can be a portion of a larger vessel on which a biofilm is grown. For example, when a base with multiple projections is used for growing a biofilm, each biofilm-coated projection can be removed from the base and placed into a length of tubing to achieve the simulated endoscope device.

FIG. 5 shows an embodiment for connecting the cleaning efficacy device 210 in tandem with an endoscope. The endoscope is shown by broken lines. The device includes a second connector 150 adapted to couple the simulated endoscope device to an exit port of an endoscope. This arrangement allows for testing the exact conditions used to clean a specific endoscope.

Figure 6:
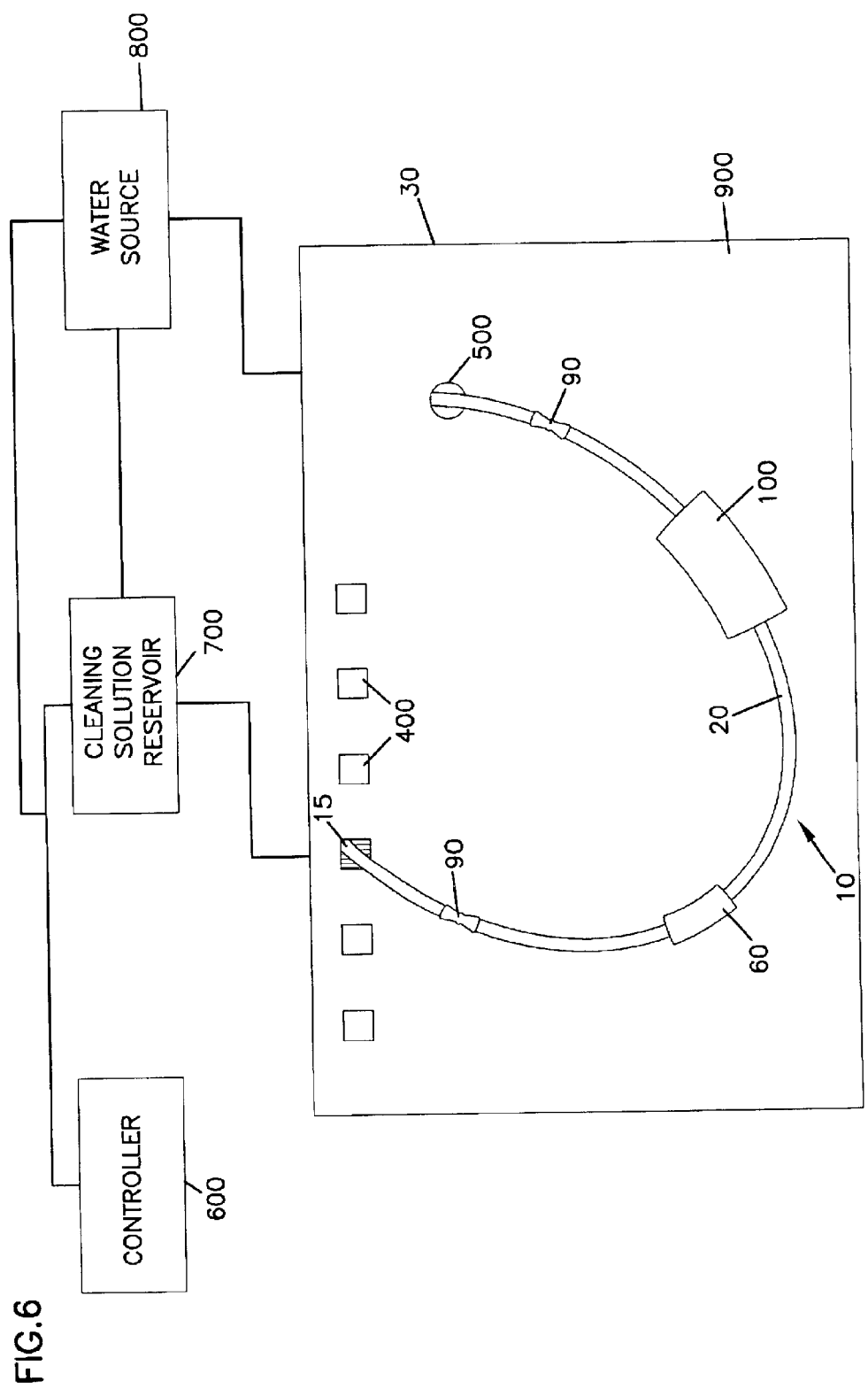
FIG. 6 is a top view of the biofilm cleaning efficacy device of FIG. 1 in place on an endoscope cleaning device.

FIG. 6 shows an embodiment in which a detector assembly 100, containing light emitting source 70 and light detector 80, is integrated into a basin-type endoscope cleaning device 30 (i.e., a reprocessor). The biofilm cleaning efficacy device 10 is shown in place in a cleaning chamber 900 connected to a port 400 on the endoscope cleaning device 30 through a hookup connector 15. The biofilm cleaning efficacy device 10 is positioned such that the biofilm chamber 40 is inside the detector assembly 100. The opposite end of the device 10 empties into a drain 500 in the endoscope cleaning device 30. The cleaning device 30 has a controller 600, a cleaning solution reservoir 700, and a water source 800. The controller 600 controls the release of cleaning solutions and water into various chambers within the reprocessor. In some embodiments, the controller 600 adjusts the temperature, pressure and amount of cleaning solutions and water entering the reprocessor chamber.

Endoscope cleaning devices, or reprocessors, generally comprise at least one cleaning chamber, at least one fluid reservoir, a fluid transfer system, and a control system. The control system selectively transfers fluid from the fluid reservoir, through the fluid transfer system, to the cleaning chamber; and selectively transfers water from a water source, through the fluid transfer system, to the cleaning chamber. The control system controls the specified pressures, volumes and timing of injecting cleaning, disinfecting, and sterilizing solutions and water through the fluid transfer system.

Another embodiment of the instant invention is a method of cleaning an endoscope involving the steps of attaching the endoscope to one port of a cleaning apparatus, attaching a simulated endoscope to a second port of the cleaning apparatus, running the cleaning and disinfecting cycle of the cleaning apparatus, and analyzing the simulated endoscope to determine the effectiveness of the cleaning cycle. The cleaning cycle is analyzed by determining the presence, absence, or amount of biofilm-specific indicator in the biofilm-containing region of the simulated endoscope. The presence or amount of biofilm-specific indicator above a predetermined level means the cleaning cycle was ineffective and the absence of or amount of biofilm-specific indicator below a predetermined level means the cleaning cycle was effective.

Another method for assessing and evaluating a cleaning process for cleaning an instrument comprises providing a simulated contaminated instrument, subjecting the simulated contaminated instrument to the cleaning process to be assessed and evaluated, and evaluating the cleaning process by analyzing the simulated instrument for the presence of remaining contamination.

Advantages of the system of the present invention include evaluating the effectiveness of a cleaning process on a simulated instrument which provides a similar internal environment to be cleaned, and may contain microorganisms similar to those expected to be present in the instruments to be cleaned. Another advantage provided by the instant invention is the ability to select the optimum cleaning conditions and the optimum cleaning agents and processes for cleaning a particular instrument.

An alternative design is to connect the biofilm cleaning efficacy monitor downstream from medical devices undergoing reprocessing. This design has the advantage of monitoring the output of a device reprocessor in a worst-case situation, whereby the effluent of a reprocessed device is used for biofilm cleaning efficacy monitoring. This "in-series" design could be constructed with the biofilm cleaning efficacy monitor either within or outside of the medical device reprocessor.

The above specification provides a complete description of the manufacture and use of the device of the invention. Since many embodiments of the invention can be made without departing from the spirit and scope of the invention, the invention resides in the claims hereinafter appended.

What is claimed is:

1. A method for assessing and evaluating a cleaning process comprising:
   providing biofilm matrices on a support;
   subjecting the support and biofilm matrices to the cleaning process to be assessed and evaluated; and
   evaluating the cleaning process by analyzing the support for the presence of remaining biofilm matrices, including:
   contacting the support with a biofilm-specific indicator and detecting any indicator present on the support.

2. The method of claim 1, wherein the cleaning process includes a decontamination process selected from the group consisting of washing, disinfecting, sterilizing, and combinations thereof.

3. The method of claim 1, wherein the support is a portion of an interior of a simulated endoscope.

4. The method of claim 1, wherein the support is positioned inside a simulated endoscope.

5. The method of claim 1, wherein the support comprises a chamber containing the biofilm, wherein the chamber is attached to and in fluid communication with a simulated endoscope.

6. The method of claim 5, wherein the chamber has known light transmitting or light absorbing properties, and the step of analyzing the support for the presence of remaining biofilm comprises passing a light beam through the chamber and detecting the transmitted or absorbed light; wherein a change from the known properties in the transmitted or absorbed light is indicative of the presence of biofilm matrices.

7. The method of claim 1, wherein the biofilm-specific indicator is a biofilm-specific dye and the detecting step comprises directing a dye-specific light source at the support and receiving light emitted or transmitted by the dye in a light detector.

8. The method of claim 1, wherein the indicator specifically binds a polysaaccharide component of the biofilm matrices.

9. A method for assessing and evaluating a cleaning process comprising:
   (a) contaminating a support with a known biofilm, the biofilm including biofilm matrices, the support generating at least one support spectral band and the biofilm matrices generating at least one biofilm spectral band when illuminated by light;
   (b) subjecting the support and the biofilm matrices to the cleaning process to be assessed and evaluated; and
   (c) evaluating the cleaning process by evaluating the support for remaining biofilm matrices by spectroscopic analysis including:
     (i) contacting the support with a biofilm-specific indicator;
     (ii) illuminating the support with light;
     (iii) receiving light reflected from the support;
     (iv) generating an electrical signal indicative of the support and the biofilm-specific indicator;
     (v) separating components of the electrical signal attributable to the at least one support spectral band and the at least one biofilm-specific indicator spectral band; and
     (vi) analyzing the components of said electrical signal attributable to each of said spectral bands to generate an output display representative of residual biofilm matrices remaining on said support after said cleaning process.

10. The method of claim 9, wherein the light is in the infrared range.

11. The method of claim 9, wherein the light is in the ultraviolet range.

12. A cleaning efficacy system comprising:
   a simulated endoscope comprising a length of tubing having at least one lumen, a biofilm coating including biofilm matrices, a biofilm-specific indicator, and at least one filter, wherein the biofilm coating, biofilm-specific indicator and filter are in fluid communication with the tubing;
   a light source selected to detect the biofilm-specific indicator; and
   a light detector selected to detect light from the light source;
   wherein the biofilm-specific indicator specifically binds to the biofilm matrices of the biofilm coating.

13. A simulated endoscope device comprising:
   a length of tubing, the tubing having at least one lumen;
   a biofilm coating including biofilm matrices; and
   a biofilm-specific indicator, the biofilm coating and the biofilm-specific indicator being in fluid communication with the tubing;
   wherein the biofilm-specific indicator specifically binds to the biofilm matrices of the biofilm coating.

14. The simulated endoscope device of claim 13, further comprising at least one filter for preventing portions of the biofilm coating from exiting the tubing; wherein the at least one filter is in fluid communication with the tubing.

15. The device of claim 13, wherein the tubing is transparent and flexible.

16. The device of claim 13, wherein the tubing is adapted for connection to an endoscope cleaning device.

17. The device of claim 13, further comprising a first connector attached to one end of the tubing, the first connector adapted to couple the simulated endoscope device to an endoscope cleaning device.

18. The cleaning efficacy system of claim 17, further comprising a second connector, the second connector adapted to couple the simulated endoscope device to an exit port of an endoscope.

19. The device of claim 13, wherein the simulated endoscope device is disposable.

20. The device of claim 13, wherein the biofilm-specific indicator is provided in a frangible chamber.

21. The device of claim 20, wherein the frangible chamber is inside the tubing.

22. The device of claim 13, wherein the biofilm coating is present on an inner surface of the tubing.

23. The device of claim 13, wherein the biofilm coating is present on a support contained within the tubing.

24. An endoscope cleaning assembly comprising:
   a) an endoscope cleaning device comprising at least one cleaning chamber, at least one fluid reservoir, a fluid transfer system, and a control system; wherein the control system selectively transfers fluid from the fluid reservoir, through the fluid transfer system, to the cleaning chamber, and selectively transfers water from a water source, through the fluid transfer system, to the cleaning chamber;
   b) a simulated endoscope device comprising hollow tubing, a biofilm coating including biofilm matrices, a biofilm-specific indicator that specifically binds to the biofilm matrices of the biofilm coating, and at least one filter; wherein the biofilm coating, biofilm-specific indicator, and filter are in fluid communication with the hollow tubing; and c) at least one connector for fluidly connecting the simulated endoscope device to the endoscope cleaning device.

25. A method of cleaning an endoscope comprising:

(a) attaching the endoscope to an endoscope cleaning device;

(b) attaching a simulated endoscope device to the endoscope cleaning device, the simulated endoscope device comprising hollow tubing having at least one lumen, a biofilm coating including biofilm matrices, a biofilm-specific indicator that specifically binds to the biofilm matrices of the biofilm coating, and at least one filter, wherein the biofilm coating, the biofilm-specific indicator, and the at least one filter are in fluid communication with the tubing;

(c) running a cleaning and disinfecting cycle of the endoscope cleaning device;

(d) analyzing the simulated endoscope device to determine the effectiveness of the cleaning cycle by determining the presence or absence of biofilm matrices after the cleaning cycle, wherein the presence of biofilm matrices indicates the cleaning cycle was ineffective; the absence of biofilm matrices indicates the cleaning cycle was effective; and (e) repeating steps (a) through (d) until the amount of biofilm detected falls below a predetermined level, indicating the endoscope is clean and disinfected.

26. A method for assessing and evaluating a cleaning process for cleaning an instrument comprising:

providing a simulated instrument contaminated with biofilm matrices, the biofilm matrices being provided on a support positioned within the simulated instrument;

subjecting the simulated contaminated instrument to the cleaning process to be assessed and evaluated; and evaluating the cleaning process by analyzing the simulated instrument for the presence of remaining biofilm matrices, including;

introducing a biofilm indicator to the support, and detecting any indicator present on the support wherein the biofilm indicator binds to extracellular portions of the biofilm matrices.

27. The method of claim 28, wherein the simulated contaminated instrument includes a length of tubing.

28. The method of claim 1, wherein the step analyzing the support for the presence of remaining biofilm matrices comprises introducing a biofilm indicator to the support, and detecting any indicator present on the support, wherein the biofilm indicator binds to extracellular portions of the biofilm matrices.

29. The method of claim 1, wherein the step analyzing the support for the presence of remaining biofilm matrices comprises breaking a frangible vial positioned inside an interior of the support to expose any remaining biofilm matrices to a biofilm indicator contained within the frangible vial.

30. A method for assessing and evaluating a cleaning process comprising:

providing biofilm matrices on a support;

subjecting the support and biofilm matrices to the cleaning process to be assessed and evaluated; and evaluating the cleaning process by analyzing the support for the presence of remaining biofilm matrices, including:

introducing a biofilm indicator to the support, and detecting any indicator present on the support, wherein the biofilm indicator binds to extracellular portions of the biofilm matrices.

* * * * *

UNITED STATES PATENT AND TRADEMARK OFFICE
CERTIFICATE OF CORRECTION

PATENT NO.    : 6,793,880 B2
DATED         : September 21, 2004
INVENTOR(S)   : Roland C. Kippenhan, Jr.

It is certified that error appears in the above-identified patent and that said Letters Patent is hereby corrected as shown below:

Column 11,
Line 22, delete "...biofilm, wherein..." and substitute -- biofilm matrices, wherein -- therefor.
Line 28, delete "...biofilm comprises..." and substitute -- biofilm matrices comprises -- therefor.
Line 39, delete "polysaaccharide" and substitute -- polysaccharide -- therefor.

Column 14,
Line 9, delete "The method of claim 28..." and substitute -- The method of claim 26 -- therefor.

Signed and Sealed this

Seventeenth Day of May, 2005

JON W. DUDAS
*Director of the United States Patent and Trademark Office*